United States Patent [19]
Breda

[11] Patent Number: 5,641,972
[45] Date of Patent: Jun. 24, 1997

[54] METHOD AND A SENSOR FOR MEASURING THE CONTENT OF WATER IN THE LIQUID STATE IN A MOVING GAS

[75] Inventor: Jean-Marc Breda, Paris, France

[73] Assignee: Sextant Avionique, Meudon La Foret, France

[21] Appl. No.: 371,706

[22] Filed: Jan. 13, 1995

[30] Foreign Application Priority Data

Jan. 13, 1994 [JP] Japan ..................................... 94-00314

[51] Int. Cl.$^6$ ..................................................... G01N 15/06
[52] U.S. Cl. ............................ 250/573; 250/574; 356/338
[58] Field of Search ........................ 250/574, 573, 250/577, 237 G; 356/338, 342, 28; 73/29.01, 335.01

[56] References Cited

U.S. PATENT DOCUMENTS

| | | | |
|---|---|---|---|
| 3,835,315 | 9/1974 | Gravitt, Jr. ............................... | 250/218 |
| 4,188,121 | 2/1980 | Hirleman, Jr. et al. ................ | 356/336 |
| 4,613,938 | 9/1986 | Hansen et al. .......................... | 364/420 |
| 4,979,818 | 12/1990 | Kobayashi ............................. | 356/28 |
| 5,116,124 | 5/1992 | Huttmann .............................. | 356/342 |

FOREIGN PATENT DOCUMENTS

| | | |
|---|---|---|
| 0 467 127 | 1/1992 | European Pat. Off. . |
| 2 642 839A1 | of 1990 | France . |
| 61-172032 | 8/1986 | Japan . |
| WO90/05310 | 5/1990 | WIPO . |

OTHER PUBLICATIONS

Y. Aizu, "Principles and Development of Spatial Filtering Velocimetry", Applied Physics B 43, 209–224 (1987).

J.T. Ator, "Image–Velocity Sensing with Parallel–Slit Reticles"*, Journal of the Optical Society of American, vol. 53, No. 12, Dec. 1963.

J. Ritonga, T. Ushizaka and T. Asakura, "Measurements of Two–Dimensional Vector Velocity Using Image Fiber Bundle and Two Rotating Gratings", J. Optics (Paris) 1989, vol. 20, No. 3, pp. 145–156.

James C.F. Wang and Daniel A. Tichenor, "Particle Size Measurements Using an Optical Variable–Frequency–Grid Technique, Applied Optics", vol. 20, No. 8,15 Apr. 1981.

IBM Technical Disclosure Bulletin, "Improved Detection of Contaminating Particles in Fluids", vol. 28, No. 1, Jun. 1985.

Y. Aizu and K. Ogino "A Laser Velocimeter Using a Random Pattern", 2319 Optics communications 64 (1987) 1 Nov. No. 3, Amsterdam, The Netherlands.

*Primary Examiner*—Stephone Allen
*Attorney, Agent, or Firm*—Lowe, Price, LeBlanc & Becker

[57] ABSTRACT

A sensor for measuring the concentration of water in liquid phase in a gas moving relative to the sensor. The sensor itself comprises a device for illuminating the water drops transiting a measurement volume, an optical screen, a device imaging the measurement volume onto the optical screen, and photo-detectors to sense the light radiation transmitted by the optical screen.

11 Claims, 3 Drawing Sheets

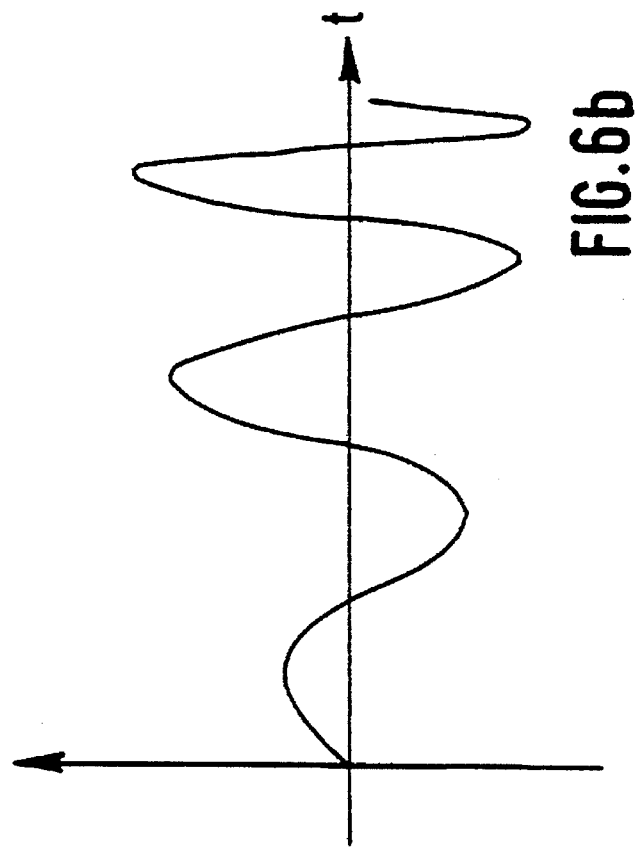
FIG.6a
FIG.6b
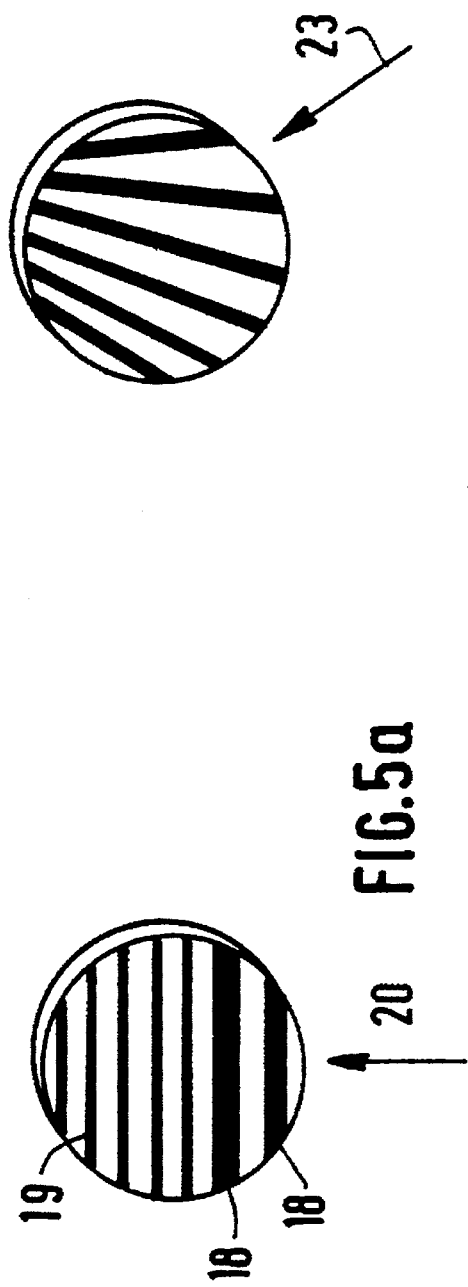
FIG.5a
FIG.5b

METHOD AND A SENSOR FOR MEASURING THE CONTENT OF WATER IN THE LIQUID STATE IN A MOVING GAS

TECHNICAL FIELD

The present invention concerns a sensor for measuring the concentration of water in the liquid state of a gas moving relative to the sensor. In particular, it applies to ascertaining the icing severity encountered by an aircraft.

DESCRIPTION OF THE RELATED ART

An aircraft pilot must know the icing conditions both to avert danger zones and to initiate de-icing. Ice accumulating in particular on the wing leading edges or on the tail unit or at the engine intakes makes the aircraft heavier and thereby degrades performance, further entailing a loss of lift which may go as far as stalling and thus engine flameout.

Icing occurs when passing through clouds in particular conditions.

In the first place, nothing happens when passing through a cloud with water in ice form. Icing only can take place when passing through a cloud consisting of liquid-water drops. Moreover the static temperature must be below 0° C., in which case the liquid then is supercooled. Lastly the supercooled concentration of water in the liquid state must be sufficient and the aircraft skin temperature also must be negative.

Presently known devices sensing the extent of icing danger generally are based on the rate at which ice accumulates.

In a first type of such devices, the ice is allowed to accumulate on a bar projecting from said device and made to vibrate. The vibration frequency is a function of the thickness of the ice on the bar and is inversely proportional to the ice thickness. When the vibration frequency reaches a given threshold, the bar is heated, whereby the ice melts and hence the frequency rises. Once the frequency is at a nominal value, heating is interrupted, ice accumulates again and hence the vibration frequency drops again. The time of such a cycle, that is the interval between two heating initiations, therefore reflects the ice-accumulation rate and hence the severity of icing conditions.

In another type of devices, holes communicating with a manometer are present in the surface of a member projecting from the aircraft; this device also includes a heating system. Ice accumulation progressively clogs the holes and consequently the pressure recorded by the manometer drops. When this pressure drops to a lower threshold, the device is heated to eliminate the ice and the said heating is interrupted when the pressure again reaches an upper threshold. As before, the time interval between two heating initiations reflects the rate of ice accumulation and thereby the severity of the icing conditions.

The above devices incur a number of drawbacks.

In the first place, their response time is very long, roughly a minute: at least two heating cycles must elapse to determine the time separating them. Moreover no information is available during heating.

Furthermore and by definition, they are inoperative if the temperature is above 0° C., since no ice then accumulates. Now icing conditions may be severe even at when above 0° C., since elsewhere at the aircraft, the temperature may be below 0° C. (for instance at an air intake where expansion takes place).

SUMMARY OF THE INVENTION

The object of the present invention is palliation of said drawbacks by providing means allowing to ascertain the concentration of water in the liquid state, said concentration together with the temperature constituting one of the essential criteria of icing danger.

For that purpose one aspect of the present invention is a method for measuring the concentration of water in the liquid state in a moving gas, said method being characterized in that it comprises the following stages:

the water drops crossing a measurement volume are illuminated so that the measurement volume can be imaged on an optical screen, the light radiation transmitted by the optical screen is detected, and the detected radiation leads to inferring said concentration.

When a water droplet passes through the measurement volume, it will backscatter some light. Accordingly its image on the optical screen will be a moving point of light. Consequently the photodetector will pick up a time-modulated light signal.

The rate at which a water droplet appears inside the measurement volume depends on the number of droplets per unit volume. Furthermore the amplitude of the modulated signal depends on the droplet sizes. The water concentration may be inferred therefore from these two parameters, and the sensor of the invention also allows ascertaining a third parameter in the form of the relative speed of the drops relative to the sensor. This speed in fact is directly related to the modulation frequency of the signal incident on the photodetector.

It should be borne in mind that somewhat similar procedures are used in measuring the speed of moving particles. Illustratively such procedures are described in PRINCIPLES AND DEVELOPMENT OF SPATIAL FILTERING VELOCIMETRY, Applied Physics B, Photophysics and Chemistry, vol. 43, 1987, pp 209–224 or in the European patent document A 0,467,127. However such literature does not suggest inferring the concentration from the detected radiation.

In a particular embodiment mode of the invention, the speed of the water drops is determined from the frequency of the variation of said radiation and the measurement volume is inferred therefrom. In turn, the concentration stated as the number of drops is inferred from said measurement volume and from said rate at which a drop appears in it, the average volume of a drop being determined from the amplitude of the variation of said radiation, and the concentration per unit volume is determined from the concentration stated in number of drops and from the average drop-volume.

Another aspect of the invention is a sensor measuring the concentration of water in the liquid state in the gas moving relative to said sensor which is characterized in that it comprises:

means for illuminating the water drops crossing a volume of measurement, an optical screen, means to image the measurement volume on said optical screen, photodetectors to sense the light radiation transmitted by the optical screen, and data-processing means to infer said concentration from the sensed radiation.

In particular, the data processing means may be designed to determine the speed of the water drops from the variation of the frequency of said radiation and to deduce the measurement volume in order to find the concentration stated in numbers of drops in said measurement volume and the rate at which a drop appears in this volume for the purpose of ascertaining the average volume of a drop from the amplitude of the variation of said radiation and of finding the concentration per unit volume of the said number of drops and the average drop volume.

The illuminating means may be a laser or a light-emitting diode. A coherent source is not required.

The optical screen may include at least one set of parallel opaque bars. In this case the signal will evince constant frequency with continuously variable amplitude.

In another embodiment mode, several sets of parallel opaque bars are used, where the bars of one set are not parallel to the bars of the other set. In this case the signal frequency varies abruptly when the droplet image transits from one screen zone formed by a first set of bars to another zone constituted by another set of bars. This design allows inferring the two components of the velocity of the water drop in the directions of the two sets of bars.

Moreover, the optical screen may include at least one set of opaque bars which are not mutually parallel. In this case the signal frequency varies continuously. This embodiment variation allows determining the angle of incidence of the drop path relative to the screen.

The opaque screen bars may all be of the same width. However, in a particular embodiment mode, the screen comprises opaque bars of different widths. In this case the cycle ratio, or, more generally, the ratio of the positive half-cycle durations to the negative half-cycle durations varies abruptly when the water droplet image transits from one screen zone to another. This feature allows inferring the droplet transit direction relative to the screen.

Again, another embodiment mode of the invention ensures that the water drops backscatter light along their paths, means being present to polarize this light in a variety of different directions depending on the position of the screen where said light is focussed. If the backscattered light is polarized, abrupt variation of the signal amplitude takes place as a rule when the backscattered beam transits from a zone of polarization in one direction to a zone of polarization in another direction. As a result, it is possible to distinguish between water droplets potentially resulting in icing and harmless ice particles: unlike water, ice polarizes light.

BRIEF DESCRIPTION OF THE DRAWINGS

The particular embodiment modes of the invention are elucidated below in relation to the attached drawings.

FIGS. 3a, 3b through 6a, 6b show applicable diverse optical screens and their resulting signals.

DESCRIPTION OF THE PREFERRED EMBODIMENT(S)

Figure 1:
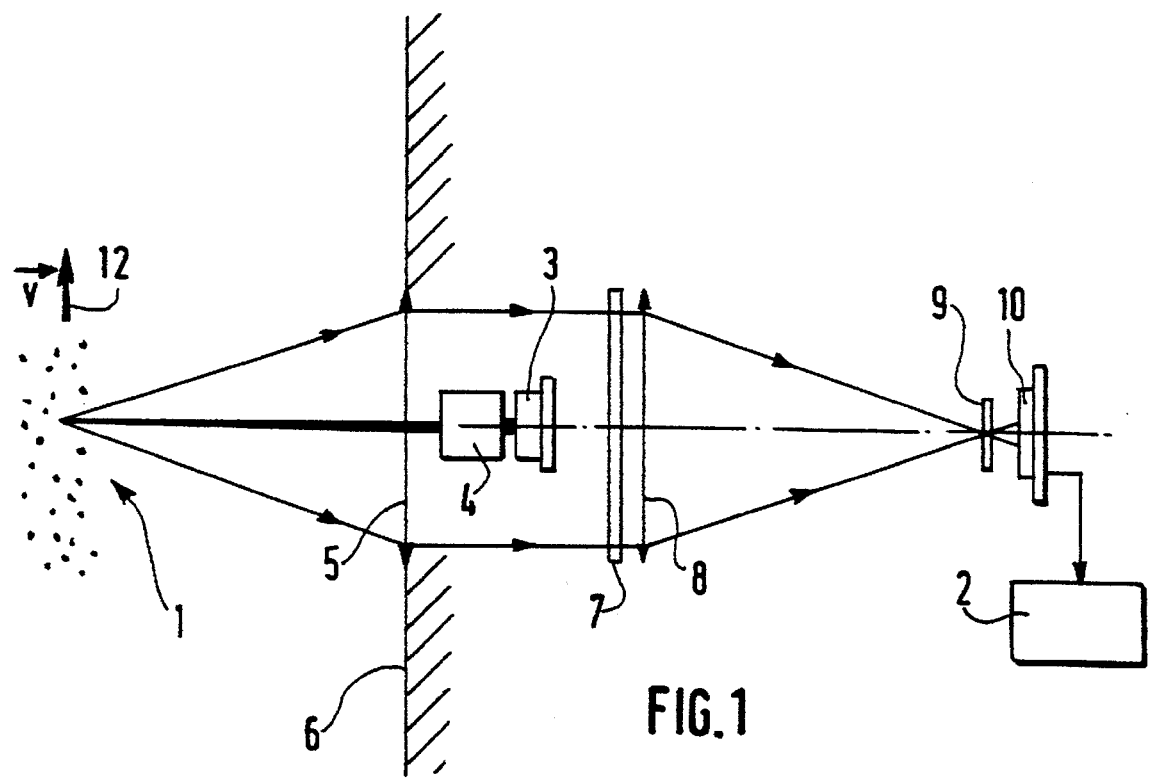
FIG. 1 shows a sensor of the invention.

Generally speaking, the sensor shown in FIG. 1 comprises a segment emitting a light beam toward a water-droplet loaded gas 1, a receiving segment and a data processor 2.

Essentially the emitting segment consists of a light source 3, for instance a laser or light-emitting diode, a collimator 4 and a lens 5.

As regards an aircraft application, the lens 5 is mounted in the plane of the aircraft skin 6. The assembly consisting of the collimator 4 and lens 5 focuses the beam from the diode 3 onto a measurement volume within the zone 1.

The lens 5 also is part of the receiving segment. The latter furthermore comprises a filter 7, a lens 8, an optical screen 9 further discussed below and a photo-detector 10 such as a photo-diode. The output of the photo-diode 10 is fed to the input of the data processor 2.

The collimator 4 and the lens 5 image the source 3 so as to form the measurement zone. This measurement zone for instance is about 10 cm from the lens 5 and evinces a diameter of about 200 μm and a length of about 1 mm. If the sensor moves through the air at speed of about 1,000 km/h, a volume of about 10 cm$^3$ typically containing several thousand water drops will be processed each second. At such a speed a water drop will transit the sensor zone in about one microsecond. Statistically therefore the measurement volume shall be devoid of drops most of the time and practically never will there be more than one drop. The data processor 2 therefore need only process one drop at a time.

Figure 2:
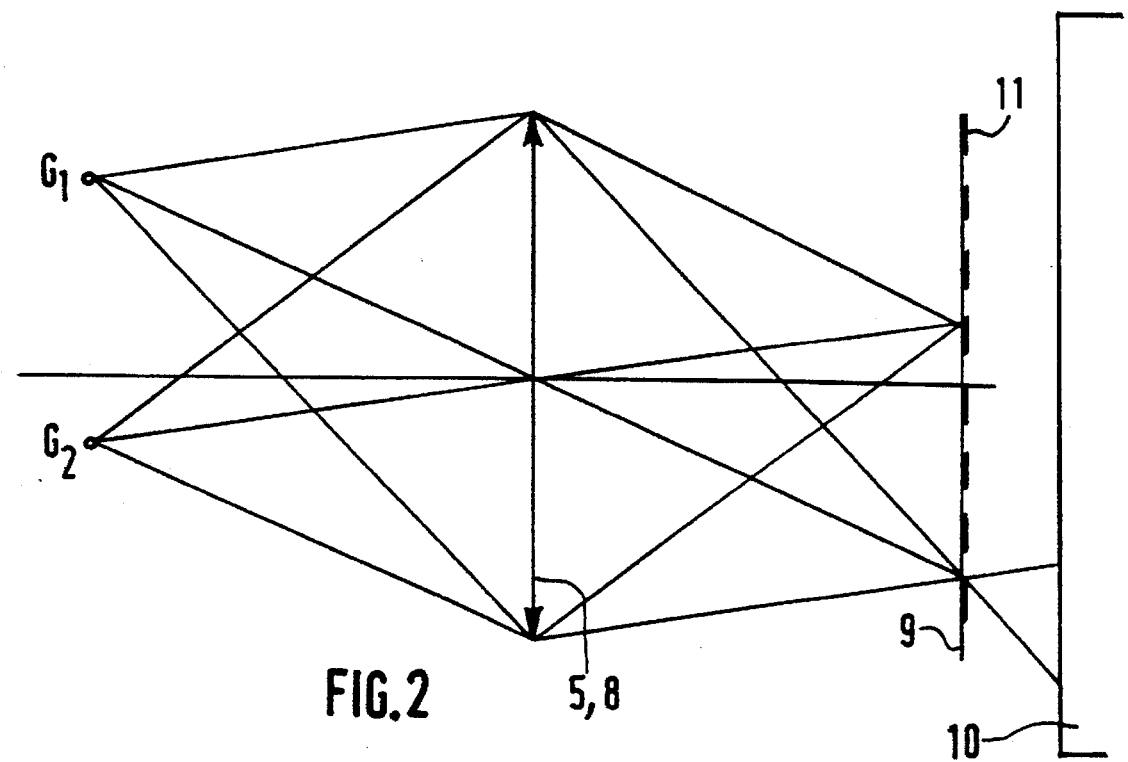
FIG. 2 shows the operation of this sensor.

The simplest optical screen 9 is that shown in FIG. 2. It consists of a set of equidistant and parallel opaque bars 11, being illustratively spaced from one another by 20 to 40 μm.

When the sensor moves at a speed V in the direction of the arrow 12 of FIG. 1, the image of a drop will move on the screen 9. Illustratively, at two consecutive times t1 and t2, a drop will be at positions G1 and G2. When at G1, the drop image is focused between two opaque bars, whereby the photo-detector 10 is illuminated. On the other hand, at G2, the drop image falls on an opaque bar and light is not transmitted.

In this embodiment mode, the output signal of the photo-detector 10 is a constant-frequency signal, said frequency depending on the inter-bar distance and of the speed V. Its amplitude is a function of the backscattered light, hence of the drop diameter and thereby of the volume of the water drop.

Once fed the signal, the data processor 2 infers the speed and hence the measurement volume. Knowing the rate at which a drop shall be present, the processor calculates the number of drops inside the volume, that is the drop concentration expressed in the number of drops. Furthermore, knowing the signal amplitude, the processor infers the size and hence the average volume of a drop. With knowledge both of the number of drops and the average volume of a drop, the processor at once calculates the concentration per unit volume of water droplets in the ambient air.

Figure 3A:
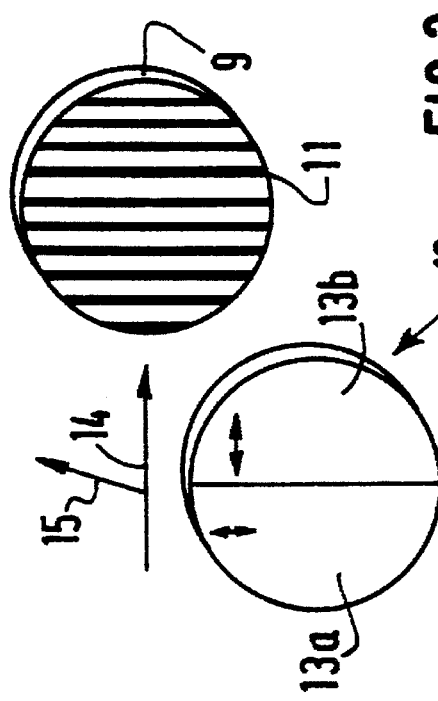
Figure 3B:
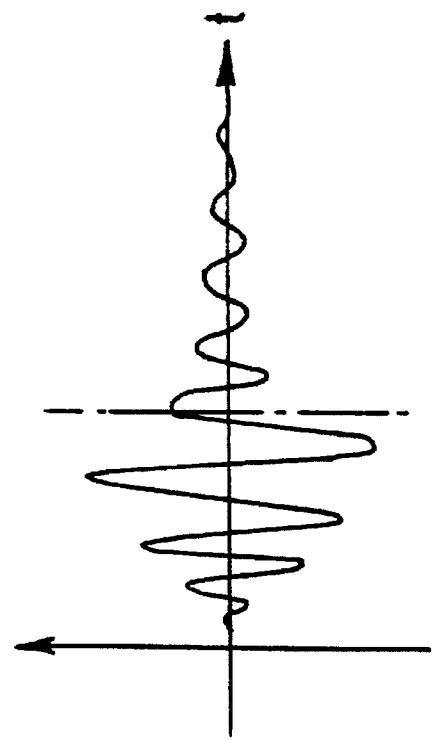

FIG. 3a shows an embodiment mode wherein a component 13 constituted by two adjoining, linear polarizers 13a and 13b of mutually perpendicular axes is present in front of the screen 9. When the image of a water drop passes through the screen 9 as shown by the arrow 14, then this image consecutively is subjected to the actions of the polarizers 13a and 13b. If the water-drop image is unpolarized, the signal will remain unaltered when passing the boundary between the two polarizers. However if this image is polarized as indicated by the arrow 15, that is, in a direction slightly different from the direction of polarization of the polarizer 13a, then this signal undergoes an abrupt drop in light intensity as it crosses the middle zone of the screen 9, as indicated by FIG. 3b.

The optical screen actually being used may be more complex than the one shown in the above Figures.

Figure 4A:
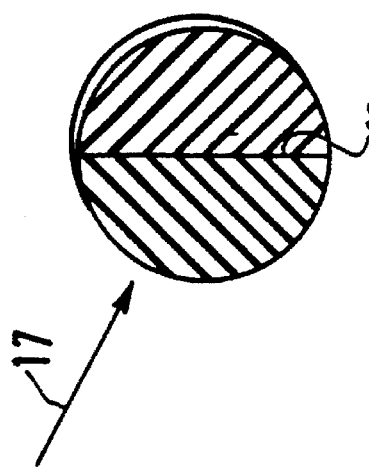

In FIG. 4a, the opaque bars run in two mutually perpendicular directions on either side of the screen middle 16, thereby forming a herringbone pattern.

Figure 4B:
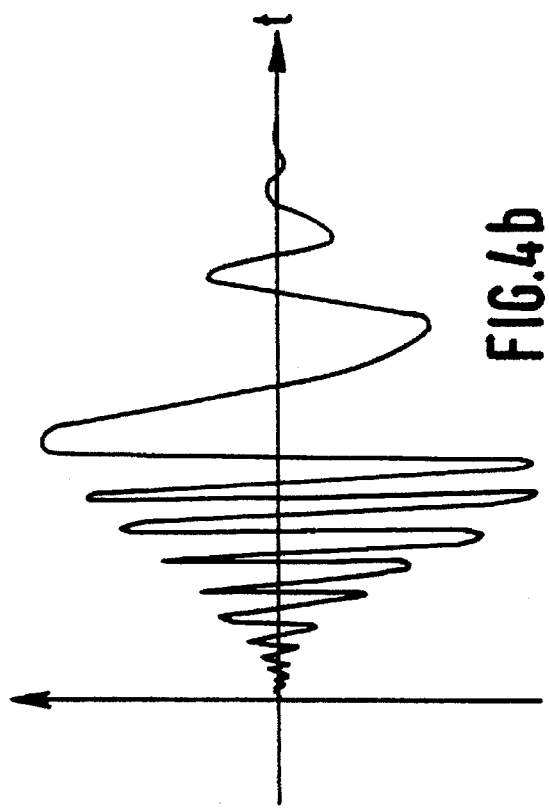

Assuming a droplet image transiting the screen in the direction of the arrow 17, that is, largely perpendicularly to the bars of the first half of the screen being crossed, a sharp decrease in frequency as shown in FIG. 4b will take place as the middle is being crossed: at constant speed, the droplet image crosses the spaces between the fringes of the first zone nearly perpendicularly and therefore very rapidly, while it crosses the spaces between the fringes of the second zone at a substantial slope and hence in a much longer time.

FIG. 5a shows the case of the first two transited bars 18 being very wide compared to the ensuing bars 19. If a drop image transits the screen in the manner of the arrow 20, the two first positive (or negative) halves 21 of the cycle shall be much longer in time than the following positive halves 22. On the other hand the negative halves shall preserve the same duration provided the gaps between the bars remain the same. In this manner it is possible to determine the direction in which a droplet transits the sensor field and consequently the direction of its velocity. Such a feature may be especially useful when measuring vertical speeds which may be negative.

As regards the case shown in FIG. 6a, the opaque bars no longer are parallel. In this embodiment mode they substantially converge outside the screen surface. If a drop transits this screen as indicated by the arrow 23, the time to pass from one opaque bar to the next shall continually decrease and hence the signal frequency shall rise as shown by FIG. 6b.

Accordingly the sensor of the invention offers many advantages.

Be it borne in mind in this respect that the sensor components are very simple ones. The light source need not be coherent, the optics aperture may be slight, and accordingly single or doublet lenses may be used, and the sensor is free of optical separators. Moreover a wide-pass filter with high transmission may be used provided that stray light be minor.

Again, the screen parameters are easily modified to match this sensor to different conditions.

The invention claimed is:

1. A method for measuring the concentration of water in the liquid state in a moving gas, comprising the steps of:

illumination water drops crossing a measurement volume to form an image of the measurement volume on an optical screen, detecting light radiation transmitted by the optical screen, and determining said concentration from the detected radiation.

2. Method defined in claim 1, wherein the speed of the water drops is determined from the frequency of the variation of said radiation and the measurement volume is deduced therefrom, the concentration stated in number of drops is determined from said measurement volume and from the rate at which a drop is present in this volume, the average drop-volume being determined from the amplitude of the variation of said radiation, and the concentration per unit volume is determined from the drop concentration stated in number of drops and from the average volume of a drop.

3. Sensor to measure the concentration of water in liquid form in a gas moving relative to said sensor, comprising:

means to illuminate water drops transiting a measurement volume, an optical screen, means to image said measurement volume on said optical screen, photo-detectors to sense the light radiation transmitted by the optical screen, and data processing means to determine said concentration of water in liquid form in a gas from the sensed radiation.

4. Sensor defined in claim 3, wherein said data processing means determine the speed of the water drops from the variation in frequency of said radiation and infer therefrom the measurement volume, deduce the concentration stated in number of drops of said measurement volume and the rate at which a drop is present in this volume, determine the average drop volume from the amplitude of the variation of said radiation, and infer the concentration per unit volume from the concentration stated in number of drops and from the average drop volume.

5. Sensor defined in claim 3, wherein the illuminating means include a light-emitting diode.

6. Sensor defined in claim 3, wherein the illuminating means include a laser diode.

7. Sensor defined in claim 3, wherein the optical screen includes at least one set of mutually parallel opaque bars.

8. Sensor defined in claim 7, wherein the optical screen comprises several sets of parallel bars, the bars of the different sets not being parallel from set to set.

9. Sensor defined in claim 3, wherein the optical screen comprises at least one set of opaque bars which are mutually non-parallel.

10. Sensor defined in claim 7, comprising bars of different widths.

11. Sensor defined in claim 3, comprising means in the path of the light backscattered by the water drops to polarize said light in a plurality of different directions depending on the screen position on which said light will be focused.

* * * * *